US007307081B2

(12) United States Patent
Miller et al.

(10) Patent No.: US 7,307,081 B2
(45) Date of Patent: *Dec. 11, 2007

(54) PIPERIDINE DERIVATIVES USEFUL AS CCR5 ANTAGONISTS

(75) Inventors: Michael W. Miller, Westfield, NJ (US); Jack D. Scott, Springfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 189 days.

This patent is subject to a terminal disclaimer.

(21) Appl. No.: 10/738,907

(22) Filed: Dec. 17, 2003

(65) Prior Publication Data

US 2004/0132711 A1 Jul. 8, 2004

Related U.S. Application Data

(60) Provisional application No. 60/434,306, filed on Dec. 18, 2002.

(51) Int. Cl.
*A61K 31/497* (2006.01)

(52) U.S. Cl. .......................... 514/252.18; 514/252.11; 514/253.11; 514/253.13; 544/295; 544/357; 544/364

(58) Field of Classification Search ............... 546/187, 546/184; 544/358, 295, 357, 364; 514/252.18, 514/252.11, 253.11, 253.13
See application file for complete search history.

(56) References Cited

U.S. PATENT DOCUMENTS

| | | | |
|---|---|---|---|
| 5,883,096 | A | 3/1999 | Lowe et al. |
| 5,889,006 | A | 3/1999 | Lowe et al. |
| 5,952,349 | A | 9/1999 | Asberom et al. |
| 5,977,138 | A | 11/1999 | Wang et al. |
| 5,994,356 | A * | 11/1999 | Pieper et al. .......... 514/252.02 |
| 6,037,352 | A | 3/2000 | Lowe et al. |
| 7,008,946 | B2 * | 3/2006 | Miller ................... 514/252.18 |

FOREIGN PATENT DOCUMENTS

WO   WO 02/079194   10/2002

OTHER PUBLICATIONS

Vlieghe et al., Journal of Medicinal Chemistry, 2001, 44, 3014.*
Cohen et al., Am. J. Clin. Pathol., 1996, 105, 589.*
A-M Vandamme, et al., Anti-human Immunodeficiency Virus Drug Combination Strategies, *Antiviral Chemistry & Chemotherapy* 9:187-203 (1998).
Bruhl et al., "Depletion of CCR5-Expressing Cells with Bispecific Antibodies and Chemokine . . . ", J. Immunology (2001), 166: 2420-2426.
Sellebjerg et al., "CCR5 (delta)32, matrix metalloproteinase-9 and disease activity in multiple sclerosis", J. of Neuroimmunology (2000), 102: 98-106.

Simpson et al., "Expression of the Beta-chemokine receptors CCR2, CCR3 and CCR5 in multiple sclerosis central nervous system tissue", J. of Neuroimmunology (2000), 108: 192-200.
Sorensen et al., "Expression of specific chemokines and chemokine receptors in the central nervous system of multiple sclerosis patients", J. of Clinical Investigation (1999), 103(6): 807-815.
Balashov et al., "CCR5 and CXCR3 T cells are increased in multiple scherosis and their ligands . . . ", Proc. Natl. Acad. Sci. (Jun. 1999), 96: 6873-6878, Immunology.
Barcellos et al., "CC-chemokine receptor 5 polymorphism and age of onset in familial multiple sclerosis", Immunogenetics (2000), 51: 281-288.
Zang et al., "Aberrant T cell migration toward RANTES and MIP-1 (alpha) in patients with multiple sclerosis . . . ", Brain (2000), 123: 1874-1882.
Schuh et al., "The role of CC chemokine receptor 5 (CCR5) and RANTES/CCL5 during chronic fungal asthma in mice", The FASEB Journal (Feb. 2002), 16: 228-230.
Yang et al., "A non-peptide CCR5 antagonist inhibits collagen-induced arthritis by modulating T cell migration without affecting anti-collagen T cell responses", Eur. J. Immunol. (2002), 32:2124-2132.
Loetscher et al., "Homing chemokines in rheumatoid arthritis", Arthritis Research (2002), 4(4): 233-236.
Zapico et al., "CCR5 (chemokine receptor-5) DNA-polymorphism influences the severity of rheumatoid arthritis", Genes and Immunity (2000), 1: 288-289.

(Continued)

*Primary Examiner*—Celia Chang
(74) *Attorney, Agent, or Firm*—Krishna G. Banerjee

(57) ABSTRACT

The present invention provides a compound of the formula

I or a pharmaceutically acceptable salt or solvate thereof, wherein the various moieties are as defined in the specification. The present invention also provides pharmaceutical compositions containing the compound of this invention, and methods of treatment using the compound of this invention. The invention also relates to the use of a combination of a compound of this invention and one or more antiviral or other agents useful in the treatment of Human Immunodeficiency Virus (HIV). The invention further relates to the use of a compound of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

17 Claims, No Drawings

OTHER PUBLICATIONS

Scheerens et al., "Characterization of chemokines and chemokine receptors in two murine models of inflammatory bowel disease . . . ", Eur. J. Immunol. (2001), 31: 1465-1474.

Horuk et al., "Chemokine Receptor Antagonists", John Wiley & Sons, Inc. Med. Res. Rev. (2000), 20(2): 155-168.

Fischereder et al., "CC chemokine receptor 5 and renal-transplant survival", The Lancet (Jun. 2, 2001), 357: 1758-1761.

Murai et al., "Active participation of CCR5 CD8 T lymphocytes in the pathogensis of liver injury in graft-versus-host disease", J. of Clinical Investigation (Jul. 1999), 104(1): 49-57.

J. Michael Kilby, "Therapeutic potential of blocking HIV entry into cells: focus on membrane fusion inhibitors", Exp. Opin. Invest. Drugs (1999), 8(8): 1157-1170.

Mastrolorenzo et al., "Small molecule antagonists of chemokine receptors as emerging anti-HIV agents", Expert Opin. Ther. Patents (2001), 11(8): 1245-1252.

Agrawal et al., "Chemokine receptors: emerging opportunities for new anti-HIV therapies", Expert Opin. Ther. Targets (2001), 5(3): 303-326.

* cited by examiner

PIPERIDINE DERIVATIVES USEFUL AS CCR5 ANTAGONISTS

PRIORITY APPLICATION

This application claims priority to U.S. provisional patent application, Ser. No. 60/434,306 filed Dec. 18, 2002.

FIELD OF THE INVENTION

The present invention relates to piperidine derivatives useful as selective CCR5 antagonists, pharmaceutical compositions containing the compound of this invention, and methods of treatment using the inventive compounds. The invention also relates to the use of a combination of the compound of this invention and one or more antiviral or other agents useful in the treatment of Human Immunodeficiency Virus (HIV). The invention further relates to the use of the compound of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

BACKGROUND OF INVENTION

The global health crisis caused by HIV, the causative agent of Acquired Immunodeficiency Syndrome (AIDS), is unquestioned. While recent advances in drug therapies have been successful in slowing the progression of AIDS, there is still a need to find a safer, more efficient, less expensive way to control the virus.

It has been reported that the CCR5 gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV into the cell is CCR5. Therefore, interfering with the interaction between the viral receptor CCR5 and HIV can block HIV entry into the cell. The present invention relates to small molecules which are CCR5 antagonists.

CCR5 receptors have been reported to mediate cell transfer in inflammatory diseases such as arthritis, rheumatoid arthritis, atopic dermatitis, psoriasis, asthma and allergies. Inhibitors of such receptors are expected to be useful in the treatment of such diseases, and in the treatment of other inflammatory diseases or conditions such as inflammatory bowel disease, multiple sclerosis, solid organ transplant rejection and graft v. host disease. WO 02/791194 discloses other piperidine derivatives useful as CCR5 antagonists.

Other piperidine derivatives, which are muscarinic antagonists useful in the treatment of cognitive disorders such as Alzheimer's disease, are disclosed in U.S. Pat. Nos. 5,883,096, 6,037,352, 5,889,006, 5,952,349, and 5,977,138.

A-M. Vandamme et al., *Antiviral Chemistry & Chemotherapy*, 9:187-203 (1998) disclose current clinical treatments of HIV-1 infections in man including at least triple drug combinations or so-called Highly Active Antiretroviral Therapy ("HAART"). HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and the progression of HIV-1 to AIDS. However, these multidrug therapies do not eliminate HIV-1 and long-term treatment usually results in multidrug resistance. Development of new drug therapies to provide better HIV-1 treatment remains a priority.

SUMMARY OF THE INVENTION

The present invention provides a novel class of compounds as antagonists of the CCR5 receptor, methods of preparing such compounds, pharmaceutical compositions containing one or more such compounds, and methods of treatment, prevention or amelioration of one or more diseases associated with the CCR5 receptor.

One aspect of the invention relates to a compound having the general structure shown in Formula I:

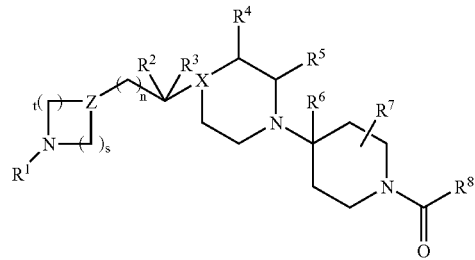

Formula I or a pharmaceutically acceptable salt or solvate thereof; wherein:

n is 0, 1, 2, 3 or 4;

s is 0, 1, 2, 3 or 4;

t is 1, 2, 3 or 4 with the provisos that i) when n is 0 and s is 2, then t is 1, 3 or 4; and ii) when n is 0 and t is 2, then s is 0, 1, 3 or 4;

X and Z can be the same or different with each being independently N or CH;

$R^1$ is H, alkyl, aralkyl, —S($O_2$)alkyl, —S($O_2$)aryl, —C(O)alkyl, —C(O)aryl, -alkyl-aryl-$R^8$, -alkyl-heteroaryl-$R^8$, —S($O_2$)cycloalkyl, —S($O_2$)-aryl-$R^8$, —C(O)cycloalkyl, —C(O)-aryl-$R^8$, —C(O)$NR^{20}R^{21}$ or —S($O_2$)$NR^{20}R^{21}$;

$R^2$, $R^4$, $R^5$, $R^6$ and $R^7$ can be the same or different each being independently H or alkyl;

$R^3$ is H, alkyl, cycloalkyl, aralkyl, heteroaralkyl, aryl or heteroaryl;

or R and $R^3$ taken together are =N(O-alkyl), =N(OH), =N—N($R^{20}R^{21}$) or =CH(alkyl) provided that when one or both of X and Z is N, $R^2$ and $R^3$ together are not =CH(alkyl);

$R^8$ is aryl, heteroaryl, fluorenyl; and diphenylmethyl, heteroaryl-N—

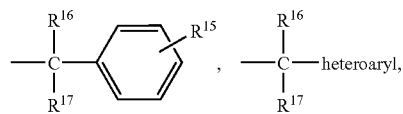

-continued

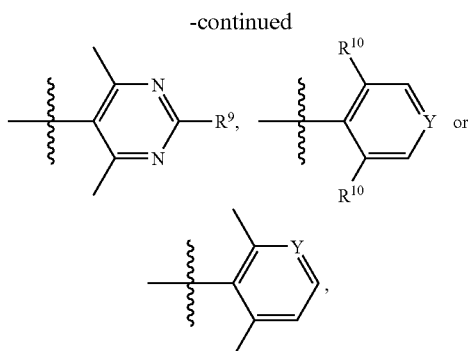

wherein each $R^{10}$ is the same or different and independently selected from —$CH_3$ or halogen, Y is N or N(→O) and each of said aryl, fluorenyl, diphenyl and heteroaryl is substituted or optionally independently substituted with 1 to 4 substituents which substituents can be the same or different each being independently selected from the group consisting of $R^{11}$, $R^{12}$, $R^{13}$, $R^{14}$ and $R^{15}$;

$R^9$ is H, alkyl, —$CF_3$, cycloalkyl, —OH, —$OCH_3$, —$NH_2$, —N(H)C(O)N(H)alkyl, —NHS($O_2$)$R^{20}$ or —N(H)C(O)alkyl;

$R^{11}$ and $R^{12}$ can be the same or different and are each independently selected from the group consisting of alkyl, haloalkyl, halogen, —$NR^{18}R^{19}$, —OH, —$CF_3$, —$OCH_3$, —O-acyl and —$OCF_3$;

$R^{13}$ is selected from the group consisting of H, $R^{11}$, aryl, —$NO_2$, —CN, —$CH_2F$, —$CHF_2$, —C(O)H, —CH=$NOR^{18}$, pyridyl-N-oxide, pyrimidinyl, pyrazinyl, —N($R^{19}$)$CONR^{19}R^{20}$, —N(H)C(O)N(H)(haloalkyl), —N(H)C(O)N(H)(cycloalkylalkyl), —N(H)C(O)alkyl, —N(H)C(O)$CF_3$, —N(H)S($O_2$)N(alkyl)$_2$, —N(H)S($O_2$)alkyl, —N(S($O_2$)$CF_3$)$_2$, —N(H)C(O)Oalkyl, cycloalkyl, —$SR^{21}$, —S(O)$R^{21}$, —S($O_2$)$R^{21}$, —S($O_2$)N(H)(alkyl), —OS($O_2$)alkyl, —OS($O_2$)$CF_3$, hydroxyalkyl, —C(O)$NR^{18}R^{19}$, —C(O)N($CH_2CH_2$—O—$CH_3$)$_2$, —OC(O)N(H)alkyl, —$CO_2R^{18}$, —Si($CH_3$)$_3$ and —B(OC($CH_3$)$_2$)$_2$;

$R^{14}$ is selected from the group consisting of alkyl, haloalkyl, $NH_2$ and $R^{15}$-phenyl;

$R^{15}$ is 1 to 3 substituents selected from the group consisting of H, alkyl, haloalkyl, —$CF_3$, —$CO_2R^{19}$, —CN, alkoxy and halogen; wherein said $R^{15}$ moieties can be the same or different each being independently selected when there are more than one $R^{15}$ present;

$R^{16}$ and $R^{17}$ can be the same or different each being independently selected from the group consisting of hydrogen and alkyl, or $R^{16}$ and $R^{17}$ together are an alkylene group and with the carbon to which they are attached form a spiro ring of 3 to 6 carbon atoms; $R^{18}$, $R^{19}$ and $R^{20}$ can each be the same or different and are each independently selected from the group consisting of H, alkyl, cycloalkyl, aryl and heteroaryl; and $R^{21}$ is selected from the group consisting of alkyl, haloalkyl, hydroxyalkyl, alkylene, cycloalkyl, aryl and aralkyl;

wherein each of said alkyl, alkylene, aryl, arylalkyl, aralkyl, alkoxy, hydroxyalkyl, heteroaryl, heteroaralkyl, cycloalkylalkyl and cycloalkyl in the definitions above can be unsubstituted or optionally independently substituted with one or more moieties which can be the same or different, where said moieties are independently selected from the group consisting of —OH, alkoxy, —CN, halogen, —$NR^{18}R^{19}$, —C(O)$NR^{18}R^{19}$, —N($R^{18}$)C(O)$R^{19}$, —N($R^{18}$)S($O_2$)$R^{19}$, —S($O_2$)$NR^{18}R^{19}$, —C(O)$OR^{18}$, —$OCF_3$, —$CF_3$, —S($O^2$)$R^{18}$ and —C(O)$R^{18}$.

Another aspect of the invention relates to a pharmaceutical composition for treatment of HIV comprising one or more compounds of formula I.

Yet another aspect of the invention relates to a method of treating Human Immunodeficiency Virus ("HIV") comprising administering to a patient in need of such treatment a therapeutically effective amount of one or more compounds of formula I. A further aspect of the invention relates to a method of treating solid organ transplant rejection, graft v. host disease, arthritis, rheumatoid arthritis, inflammatory bowel disease, atopic dermatitis, psoriasis, asthma, allergies or multiple sclerosis comprising administering to a patient in need of such treatment a therapeutically effective amount of one or more compounds of formula I.

Still another aspect of this invention relates to a method of treating Human Immuno-deficiency Virus comprising administering to a patient in need of such treatment the one or more compounds of formula I in combination with one or more antiviral or other agents useful in the treatment.

A further aspect of this invention relates to a method of treating solid organ transplant rejection, graft v. host disease, arthritis, rheumatoid arthritis, inflammatory bowel disease, atopic dermatitis, psoriasis, asthma or allergies comprising administering to a patient in need of such treatment one or more compounds of formula I in combination with one or more antiviral or other agents useful in the treatment.

The CCR5 antagonists and antiviral or other agents which are components of the combination can be administered in a single dosage or administered separately. A kit comprising separate dosage forms of the actives is also contemplated.

DETAILED DESCRIPTION OF THE INVENTION

In one embodiment, the present invention discloses compounds represented by structural formula I, Formula I

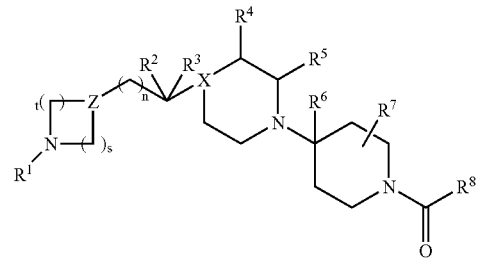

or a pharmaceutically acceptable salt or solvate thereof; wherein the various moieties are defined as above.

The compounds of formula I can be administered as racemic mixtures or enantiomerically pure compounds.

In an embodiment of the compounds of formula 1, X is CH.

In another embodiment, Z is N.

In another embodiment, t is 2 and s is 1.

In another embodiment, $R^2$, $R^5$ and $R^7$ are hydrogen.

In another embodiment, $R^4$ and $R^7$ are alkyl,

In an additional embodiment, $R^4$ and $R^7$ are methyl.

In an additional embodiment, $R^1$ is H, —S($O_2$)alkyl, —S($O_2$)aryl or —S($O_2$)cycloalkyl.

In a still additional embodiment, $R^1$ is H,

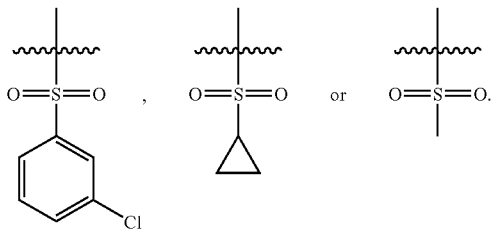

In a still additional embodiment, $R^3$ is aryl or aralkyl,

In a still another additional embodiment, $R^3$ is benzyl or phenyl and $R^8$ is heteroaryl.

In yet an additional preferred embodiment $R^8$ is

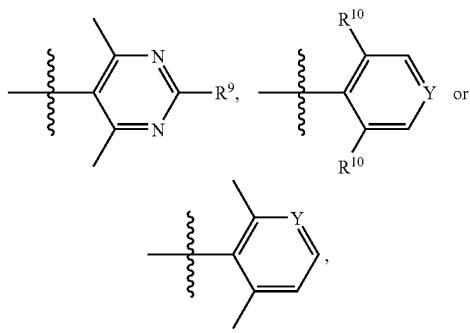

wherein each $R^{10}$ and Y is as defined.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain.

Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

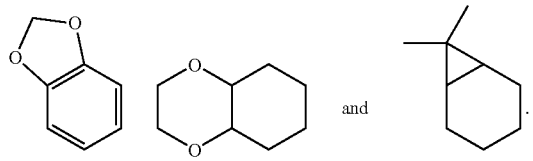

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

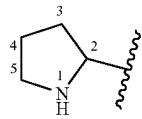

there is no —OH attached directly to carbons marked 2 and 5.

It should also be noted that tautomeric forms such as, for example, the moieties:

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR trade name from Glaxo-Wellcome Inc., Research Triangle, NC 27709; didanosine (ddI) available under the VIDEX trade name from Bristol-Myers Squibb Co., Princeton, N.J. 08543; zalcitabine (ddC) available under the HIVID trade name from Roche Pharmaceuticals, Nutley, N.J. 07110; stavudine (d4T) available under the ZERIT trademark from Bristol-Myers Squibb Co., Princeton, N.J. 08543; lamivudine (3TC) available under the EPIVIR trade name from Glaxo-Wellcome Research Triangle, NC 27709; abacavir (1592U89) disclosed in WO96/30025 and available under the ZIAGEN trademark from Glaxo-Wellcome Research Triangle, NC 27709; adefovir dipivoxil [bis(POM)-PMEA] available under the PREVON trade name from Gilead Sciences, Foster City, Calif. 94404; lobucavir (BMS-180194), a nucleoside reverse transcriptase inhibitor disclosed in EP-0358154 and EP-0736533 and under development by Bristol-Myers Squibb, Princeton, N.J. 08543; BCH-10652, a reverse transcriptase inhibitor (in the form of a racemic mixture of BCH-10618 and BCH-10619) under development by Biochem Pharma, Laval, Quebec H7V, 4A7, Canada; emitricitabine [(−)-FTC] licensed from Emory University under Emory Univ. U.S. Pat. No. 5,814,639 and under development by Triangle Pharmaceuticals, Durham, N.C. 27707; beta-L-FD4 (also called beta-L-D4C and named beta-L-2',3'-dicleoxy-5-fluoro-cytidene) licensed by Yale University to Vion Pharmaceuticals, New Haven Conn. 06511; DAPD, the purine nucleoside, (−)-beta-D-2,6,-diamino-purine dioxolane disclosed in EP 0656778 and licensed by Emory University and the University of Georgia to Triangle Pharmaceuticals, Durham, N.C. 27707; and lodenosine (FddA), 9-(2,3-dideoxy-2-fluoro-b-D-threo-pentofuranosyl)adenine, an acid stable purine-based reverse transcriptase inhibitor disclosed by the NIH and under development by U.S. Bioscience Inc., West Conshohocken, Pa. 19428.

The term "non-nucleoside reverse transcriptase inhibitors" ("NNRTI's) as used herein means non-nucleosides that inhibit the activity of HIV-1 reverse transcriptase.

Typical suitable NNRTIs include nevirapine (BI-RG-587) available under the VIRAMUNE trade name from Boehringer Ingelheim, the manufacturer for Roxane Laboratories, Columbus, Ohio 43216; delaviradine (BHAP, U-90152) available under the RESCRIPTOR trade name from Pharmacia & Upjohn Co., Bridgewater N.J. 08807; efavirenz (DMP-266) a benzoxazin-2-one disclosed in WO94/03440 and available under the SUSTIVA trade name from Dupont Pharmaceutical Co., Wilmington, Del. 19880-0723; PNU-142721, a furopyridine-thio-pyrimide under development by Pharmacia and Upjohn, Bridgewater N.J. 08807; AG-1549 (formerly Shionogi# S-1153); 5-(3,5-dichlorophenyl)-thio-4-isopropyl-1-(4-pyridyl)methyl-IH-imidazol-2-ylmethyl carbonate disclosed in WO 96/10019 and under clinical development by Agouron Pharmaceuticals, Inc., LaJolla Calif. 92037-1020; MKC-442 (1-(ethoxy-methyl)-5-(1-methylethyl)-6-(phenylmethyl)-(2,4(1H,3H)-pyrimidinedione) discovered by Mitsubishi Chemical Co. and under development by Triangle Pharmaceuticals, Durham, N.C. 27707; and (+)-calanolide A (NSC-675451) and B, coumarin derivatives disclosed in NIH U.S. Pat. No. 5,489,697, licensed to Med Chem. Research, which is co-developing (+) calanolide A with Vita-invest as an orally administrable product.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN (available from Merck) as well as nonpeptide protease inhibitors e.g., VIRACEPT (available from Agouron).

Typical suitable P is include saquinavir (Ro 31-8959) available in hard gel capsules under the INVIRASE trade name and as soft gel capsules under the FORTOVASE trade name from Roche Pharmaceuticals, Nutley, N.J. 07110-1199; ritonavir (ABT-538) available under the NORVIR trade name from Abbott Laboratories, Abbott Park, Ill. 60064; indinavir (MK-639) available under the CRIXIVAN trade name from Merck & Co., Inc., West Point, Pa. 19486-0004; nelfnavir (AG-1343) available under the VIRACEPT trade name from Agouron Pharmaceuticals, Inc., LaJolla Calif. 92037-1020; amprenavir (141W94), trade name AGENERASE, a non-peptide protease inhibitor under development by Vertex Pharmaceuticals, Inc., Cambridge, Mass. 02139-4211 and available from Glaxo-Wellcome, Research Triangle, NC under an expanded access program; lasinavir (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322623, an azapeptide under development by Bristol-Myers Squibb, Princeton, N.J. 08543, as a 2nd-generation HIV-1 PI; ABT-378 under development by Abbott, Abbott Park, Ill. 60064; and AG-1549 an orally active imidazole carbamate discovered by Shionogi (Shionogi#S-1153) and under development by Agouron Pharmaceuticals, Inc., LaJolla Calif. 92037-1020.

Other antiviral agents include hydroxyurea, ribavirin, IL-2, IL-12, pentafuside and Yissum Project No. 11607. Hydroxyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) trade name from Chiron Corp., Emeryville, Calif. 94608-2997 as a lyophilized powder for IV infusion or sc administration upon reconstitution and dilution with water; a dose of about 1 to about 20 million IU/day, sc is preferred; a dose of about 15 million IU/day, sc is more preferred. IL-12 is disclosed in WO96/25171 and is available from Roche Pharmaceuticals, Nutley, N.J. 07110-1199 and American Home Prodocts, Madison, N.J. 07940; a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein, is under preclinical development by Yissum Research Development Co., Jerusalem 91042, Israel. Ribavirin, 1-β-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include:

(a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is prefered unless there is intolerance to PIs. Drug compliance is essential. The CD4+ and HIV-1-RNA plasma levels should be monitored every 3-6 months. Should viral load plateau, a fourth drug, e.g., one PI or one NNRTI could be added. See the table below wherein typical therapies are further described:

Anti-HIV-1 Multi Drug Combination Therapies

A. Triple Combination Therapies
1. Two NRTIs[1]+one PI[2]
2. Two NRTIs[1]+one NNRTI[3]

B. Quadruple Combination Therapies[4]
Two NRTIs+one PI+a second PI or one NNRTI

C. Alternatives:[5]
Two NRTI[1]
One NRTI[5]+one PI[2]
Two PIs[6]+one NRTI[7] or NNRTI[3]
One PI[2]+one NRTI[7]+one NNRTI[3]

Footnotes to Table
1. One of the following: zidovudine+lamivudine; zidovudine+didanosine; stavudine+lamivudine; stavudine+didanosine; zidovudine+zalcitabine
2. Indinavir, nelfinavir, ritonavir or saquinavir soft gel capsules.
3. Nevirapine or delavirdine.
4. See A-M. Vandamne et al Antiviral Chemistry & Chemotherapy 9:187 at p. 193-197 and FIGS. 1+2.
5. Alternative regimens are for patients unable to take a recommended regimen because of compliance problems or toxicity, and for those who fail or relapse on a recommended regimen. Double nucleoside combinations may lead to HIV-resistance and clinical failure in many patients.
6. Most data obtained with saquinavir and ritonavir (each 400 mg bid).
7. Zidovudine, stavudine or didanosine.

Specific examples of compounds of the present invention include, but are not limited to, compounds of formula 1, wherein n is 0, t is 2, s is 1, $R^2$, $R^5$ and $R^7$ are hydrogen, $R^4$ and $R^6$ are methyl,
$R^8$ is

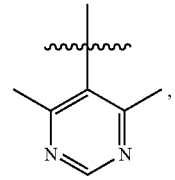

X is CH, Z is N and $R^1$ and $R^3$ are as defined in Table 1:

TABLE 1

| Example | $R^1$ | $R^3$ |
|---|---|---|
| A | ![O=S=O cyclopropyl] | ![benzyl] |
| B | PMB | ![benzyl] |
| C | ![O=S=O (3-chlorophenyl)] | ![benzyl] |

TABLE 1-continued
| Example | R¹ | R³ |
|---|---|---|
| D | H | 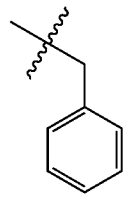 |
| E | 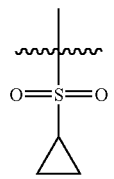 | 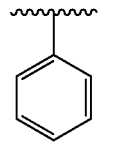 |
TABLE 1-continued
| Example | R¹ | R³ |
|---|---|---|
| F | 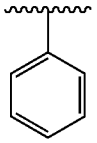 | 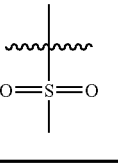 |
| G | 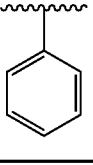 | 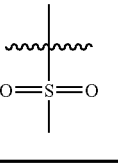 |
Illustrative compounds from Table I above are shown below in Table 1A:
TABLE 1A
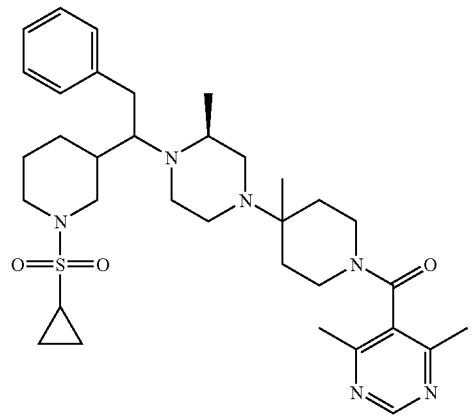
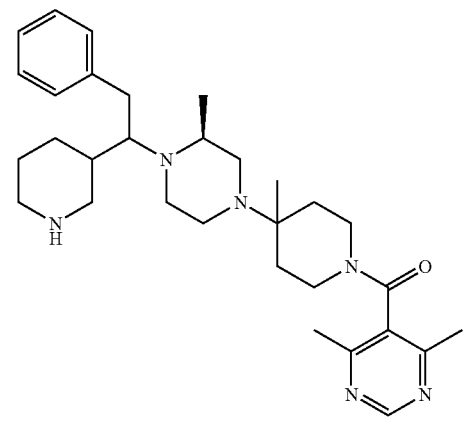

TABLE 1A-continued
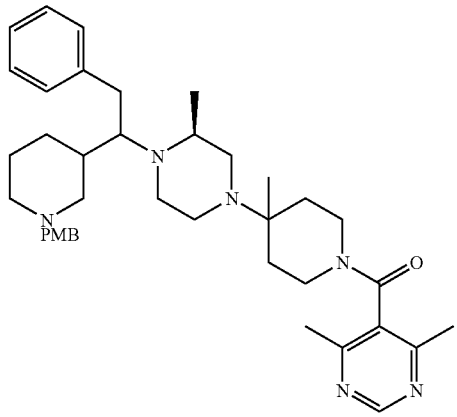
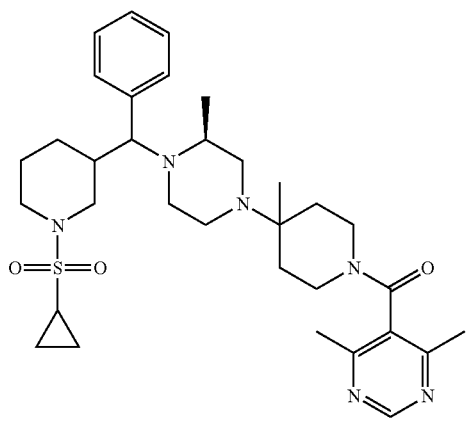
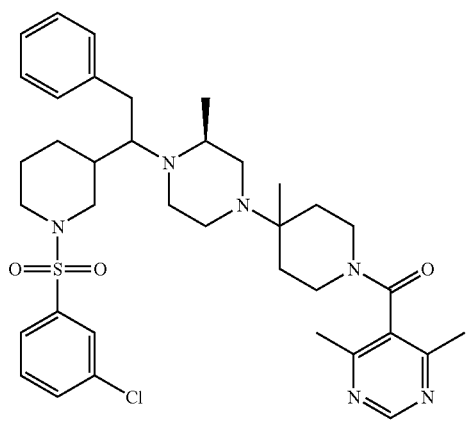

TABLE 1A-continued
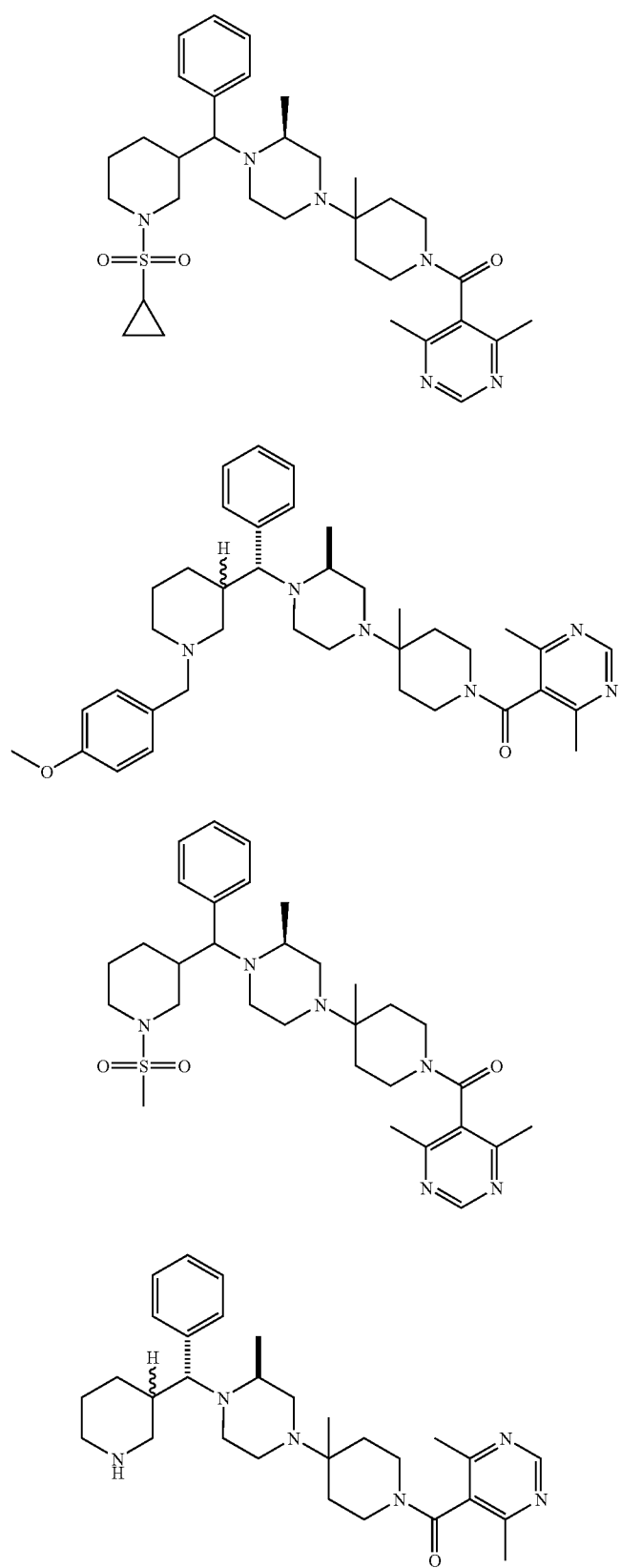

TABLE 1A-continued
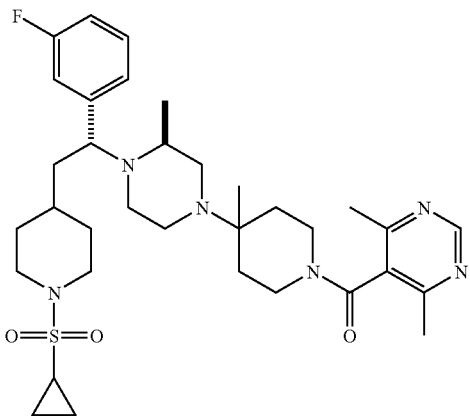
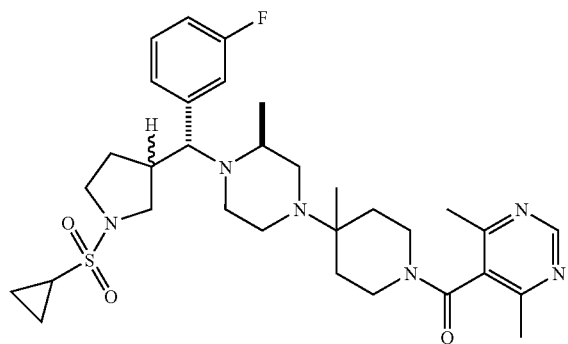
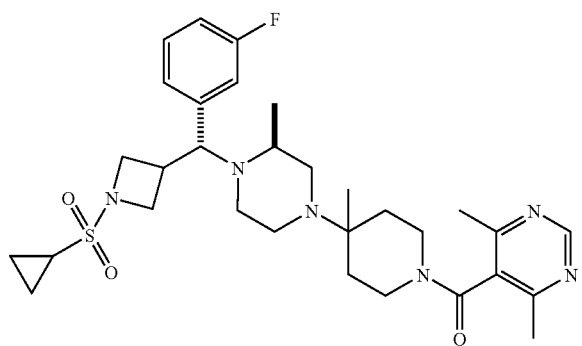
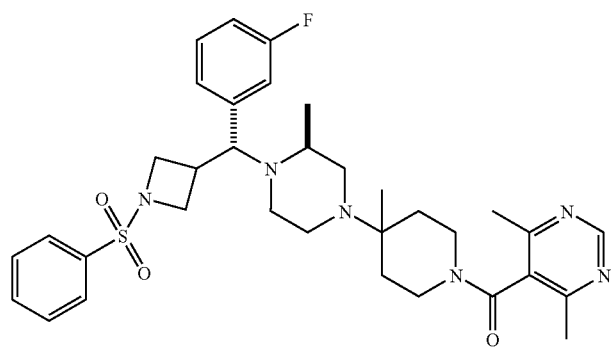

TABLE 1A-continued

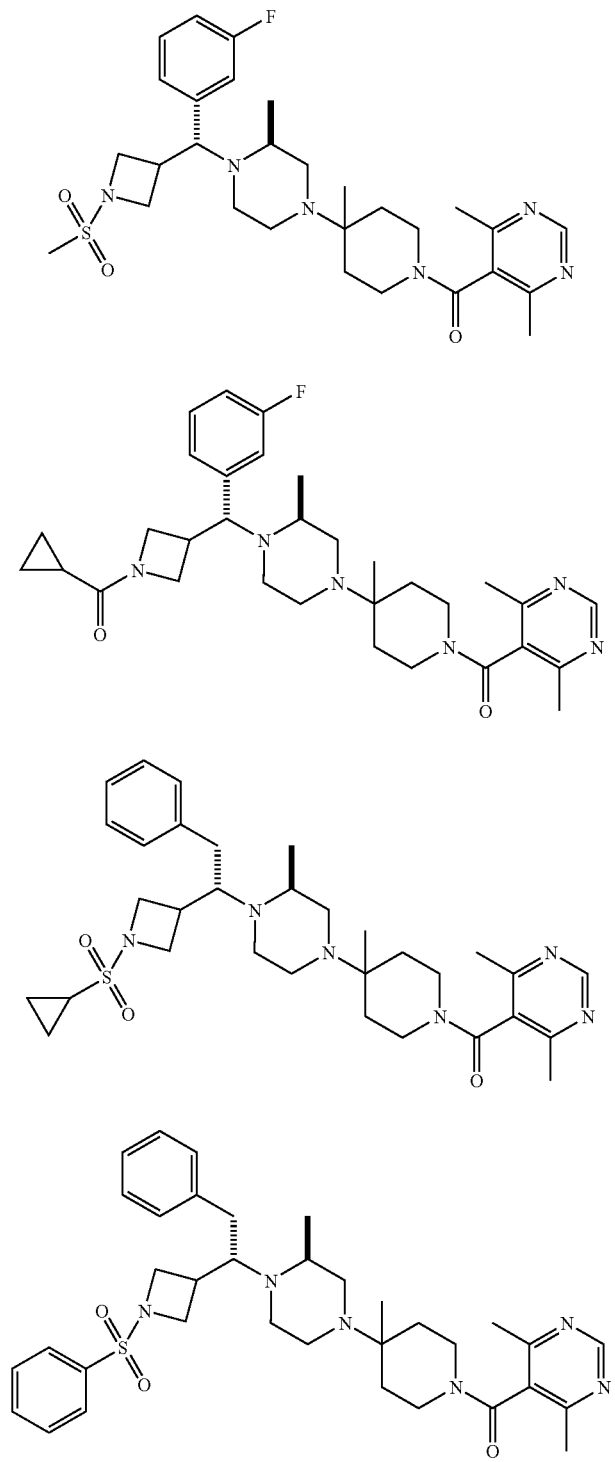

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. An example of this includes, but is not limited to, water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compound of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be deliverable subcutaneously.

Preferably the compound is administered orally.

Preferably, the pharmaceutical preparation is in a unit dosage form. In such form, the preparation is subdivided into suitably sized unit doses containing a therapeutically effective amount of the compound having formula I.

The quantity of active compound in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage of the inventive compound employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

The doses and dosage regimens of the NRTIs, NNRTIs, PIs and other agents used in combination with the compounds of this invention will be determined by the attending clinician in view of the approved doses and dosage regimens in the package inserts or as set forth in the protocols, taking into consideration the age, sex and condition of the patient and the severity of the condition treated.

In a preferred embodiment, the compound of the present invention can be used to treat Human Immunodeficiency Virus by administering to a patient in need of such treatment a therapeutically effective amount of one or more compounds having formula I, preferably in combination with one or more pharmaceutically acceptable carriers. One or more, preferably one to four, antiviral agents useful in anti-HIV-1 therapy can be used in combination with the compound of the present invention. The antiviral agent or agents can be combined with one or more compounds of the present invention in a single dosage form, or the one or more compounds of the present invention and the antiviral agent or agents may be administered simultaneously or sequentially as separate dosage forms.

The antiviral agents contemplated for use in combination with the compound of the present invention comprise nucleoside and nucleotide reverse transcriptase inhibitors, non-nucleoside reverse transcriptase inhibitors, protease inhibitors and other antiviral drugs listed below not falling within these classifications. Specific examples of antiviral agents include, but are not limited to, zidovudine, lamivudine, zalcitabine, didanosine, stavudine, abacavir, adefovir dipivoxil, lobucavir, BCH-10652, emitricitabine, beta-L-FD4, DAPD, lodenosine, nevirapine, delaviridine, efavirenz, PNU-142721, AG-1549, MKC-442, (+)-calanolide A and B, saquinavir, indinavir, ritonavir, nelfinavir, lasinavir, DMP-450, BMS-2322623, ABT-378, amprenavir, hydroxyurea, ribavirin, IL-2, IL-12, pentafuside, Yissum No. 11607 and AG-1549. In particular, the combinations known as HAART are contemplated for use in combination with the compound of this invention.

For combination treatment with more than one active agent, where the active agents are in separate dosage formulations, the active agents may be administered separately or in conjunction. In addition, the administration of one element may be prior to, concurrent to, or subsequent to the administration of the other agent.

Another aspect of the invention provides a method of treating solid organ transplant rejection, graft v. host disease, arthritis, rheumatoid arthritis, inflammatory bowel disease, atopic dermatitis, psoriasis, asthma, allergies or multiple sclerosis comprising administering to a patient in need of such treatment a therapeutically effective amount of one or more compounds of formula I, preferably in combination with one or more pharmaceutically acceptable carriers. In another embodiment, the method for treating solid organ transplant rejection, graft v. host disease, rheumatoid arthritis, inflammatory bowel disease or multiple sclerosis further comprises administering one or more other agents useful in the treatment of said diseases in combination with one or more compounds of formula I.

Agents known in the treatment of rheumatoid arthritis, transplant and graft v. host disease, inflammatory bowel disease and multiple sclerosis which can be administered in combination with the compound of the present invention are as follows:

solid organ transplant rejection and graft v. host disease:
   immune suppressants such as cyclosporine and Interleukin-10 (IL-10), tacrolimus, antilymphocyte globulin, OKT-3 antibody, and steroids;

inflammatory bowel disease: IL-10 (see U.S. Pat. No. 5,368,854), steroids and azulfidine;

rheumatoid arthritis: methotrexate, azathioprine, cyclophosphamide, steroids and mycophenolate mofetil;

multiple sclerosis: interferon-beta, interferon-alpha, and steroids.

Another aspect of the invention relates to a kit comprising in separate containers in a single package pharmaceutical composition for use in combination to treat Human Immunodeficiency Virus. In one container, a pharmaceutical composition comprises one or more compounds of formula I in one or more pharmaceutically acceptable carriers, and in separate containers, one or more pharmaceutical compositions comprising an effective amount of one or more antiviral agents or other agents useful in the treatment of Human Immunodeficiency Virus in one or more pharmaceutically acceptable carriers.

The goal of the HIV-1 therapy of the present invention is to reduce the HIV-1-RNA viral load below the detectable limit. The "detectable limit of HIV-1-RNA" in the context of the present invention means that there are fewer than about 200 to fewer than about 50 copies of HIV-1-RNA per ml of plasma of the patient as measured by quantitative, multi-cycle reverse transcriptase PCR methodology. HIV-1-RNA is preferably measured in the present invention by the methodology of Amplicor-1 Monitor 1.5 (available from Roche Diagnostics) or of Nuclisens HIV-1 QT-1.

The syntheses of the compounds useful in this invention are exemplified by the following preparative examples, which should not be construed to limit the scope of the disclosure. Alternative mechanistic pathways and analogous structures within the scope of the invention may be apparent to those skilled in the art.

The following terms may be referred to by their abbreviations in parenthesis:

para-methoxybenzyl (PMB);

dichloroethane (EDCL);

p-toluenesulfonic acid (PTSA);

Thin layer chromatography (TLC);

ethyl acetate (AcOEt or EtOAc);

sodium triacetoxyborohydride (NaBH(OAc$_3$));

di-t-butyl carbonate (BOC$_2$O);

N,N'-diisopropylethylamine (iPr$_2$NEt);

triethylamine (Et$_3$N or TEA);

butoxycarbonyl (n-Boc or Boc);

tetrahydrofuran (THF);

nuclear magnetic resonance spectroscopy (H NMR);

liquid chromatography mass spectrometry (LCMS);

high resolution mass spectrometry (HRMS);

hexane (hex);

milliliters (mL);

millimoles (mmol);

microliters (μl);

grams (g);

milligrams (mg);

room temperature (ambient) about 25° C. (rt).

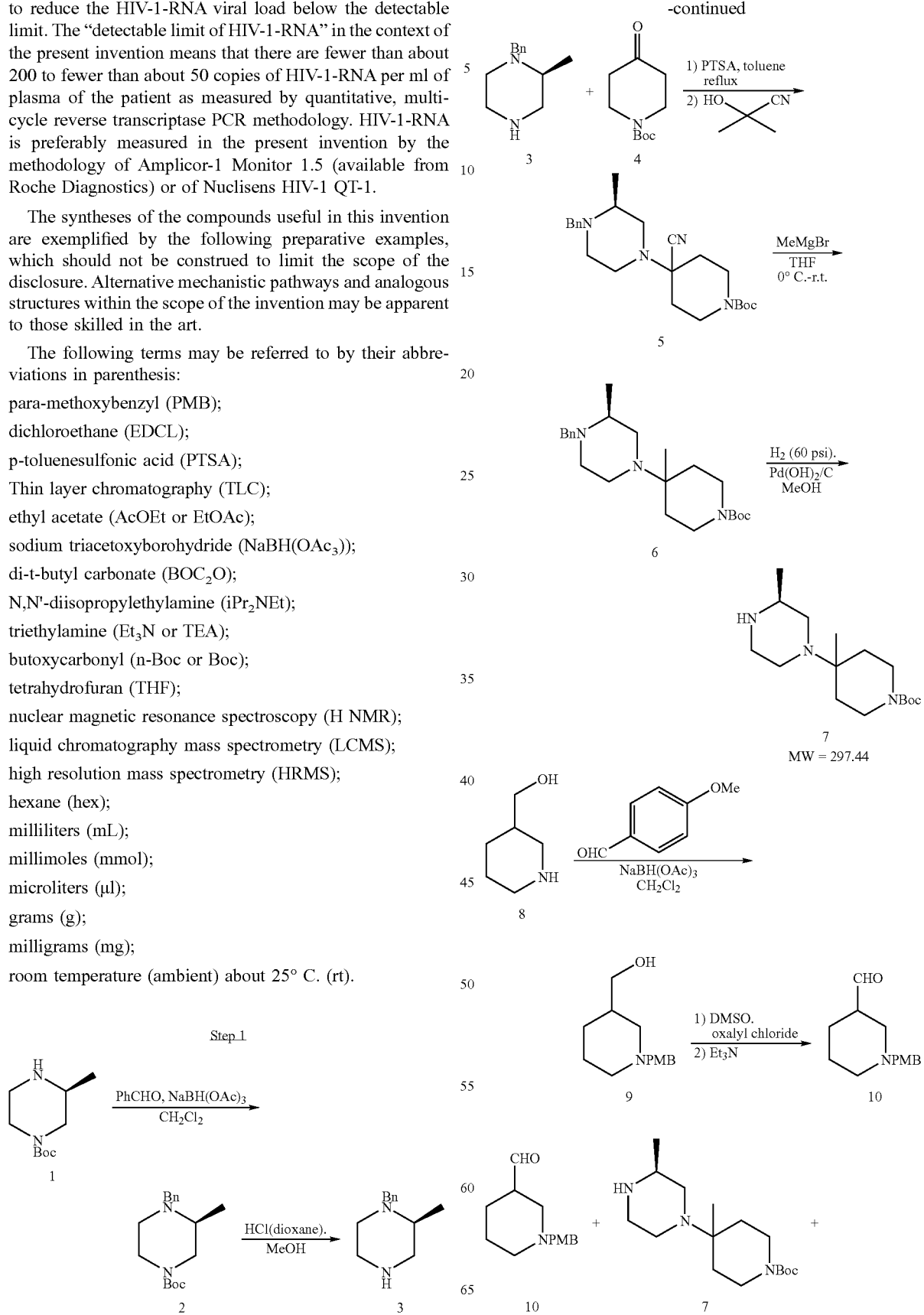

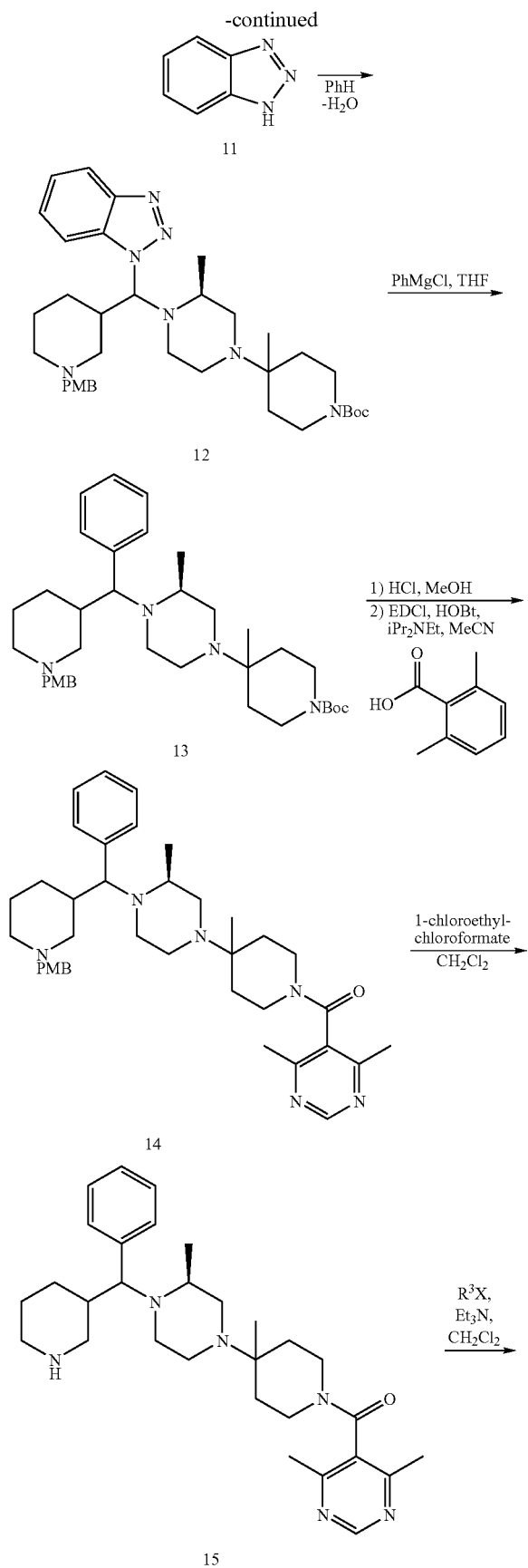

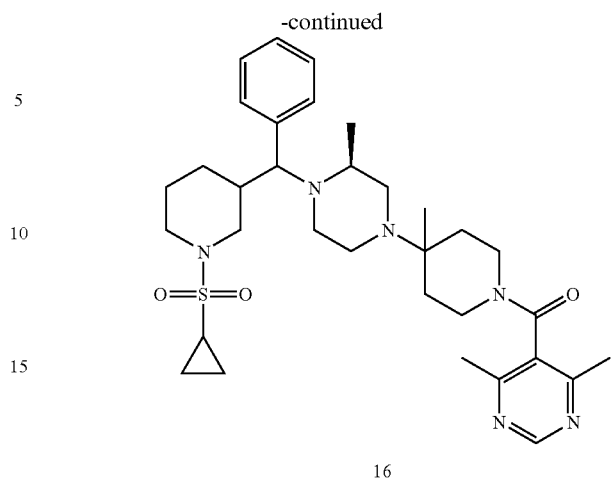

Step 1

To a solution of amine 1 (9.50 g, 47.4 mmol) in CH$_2$Cl$_2$ (150 mL) was added benzaldehyde (6.04 g, 56.9 mmol) and sodium triacetoxyborohydride (12.1 g, 56.9 mmol). The mixture was then stirred at room temperature for 16 h. The mixture was diluted with CH$_2$Cl$_2$, 1 N NaOH (aq.) was added, and the resultant mixture was stirred at room temperature for 30 min. The aqueous layer was then extracted with CH$_2$Cl$_2$ (3×). The combined organic layers were dried over Na$_2$SO$_4$, filtered, and concentrated to afford 13.8 g 2 as a yellow oil.

Step 2

To a solution of 2 (13.8 g) in MeOH (120 mL) was added 4 N HCl (in dioxane) (40 mL). The solution was stirred at room temperature for 4 h. The solution was concentrated and the crude product was partitioned between 1 N HCl and Et$_2$O. The aqueous layer was extracted with Et$_2$O (2×) and the organic layers were discarded. The aqueous layer was adjusted to pH 10 with 3 N NaOH. The aqueous layer was then extracted with CH$_2$Cl$_2$ (4×). The combined organic layers were dried over Na$_2$SO$_4$, filtered, and concentrated to afford 8.75 g 3 as a clear liquid (96% yield).

Step 3

To a solution of the amine 3 (8.75 g, 46 mmol) in toluene (100 mL) was added Boc-piperidone 4 (9.2 g, 46 mmol) and p-toluenesulfonic acid (44 mg, 0.23 mmol). The solution was heated to reflux with a Dean-Stark trap attached. The solution was stirred at reflux for 6 h. The solution was concentrated to approx. ½ the original volume. Acetone cyanohydrin (4.5 g, 52.9 mmol) was added and the solution was heated to reflux for 1 h. The solution was then cooled to 0° C. To the solution was added THF (125 mL) followed by the slow addition of methyl magnesium bromide (3M solution in Et$_2$O) (77 mL, 230 mmol). The resultant solution was stirred at 0° C. for 1 h, then continued to stir at room temperature for an additional 16 h. The mixture was poured into a mixture of ice and 25% sodium citrate solution and stirred at room temperature for 30 min. The aqueous layer was extracted with EtOAc (3×). The combined organic layers were washed with brine, dried over $Na_2SO_4$, filtered, and concentrated. The crude product was purified by flash chromatography (2:1 hexanes: EtOAc) for afford 6 (15.1 g) as a clear oil (85% yield).

Step 4

To a nitrogen degassed solution of amine 6 (6.8 g, 17.5 mmol) in MeOH (100 mL) in a pressure vessel was added palladium hydroxide on carbon (20% Pd by wt.) (1.22 g, 0.90 mmol). The vessel was sealed, purged with nitrogen, and pressurized to 60 psi with hydrogen and stirred at room temperature for 3.5 days. The solution was purged with nitrogen, filtered through Celite, and concentrated to afford 7 (5.2 g) as an off white solid (100% yield).

Step 5

To a solution of the amino alcohol 8 (10 g, 87 mmol) in $CH_2Cl_2$ (300 mL) was added p-anisaldehyde (14.2 g, 104 mmol) and sodium triacetoxyborohydride (22 g, 104 mmol) and stirred the mixture at room temperature for 16 h. The mixture was diluted with $CH_2Cl_2$. The organic layer was washed with 1 N NaOH (2×). The organic layer was then dried over $Na_2SO_4$, filtered, and concentrated. The crude product was partitioned between 3 N HCl and $Et_2O$. The aqueous layer was extracted with $Et_2O$ (2×) and the organic layers were discarded. The aqueous layer was adjusted to pH 10 with 3 N NaOH. The aqueous layer was then extracted with EtOAc (4×). The combined organic layers were washed with brine, dried over $Na_2SO_4$, filtered, and concentrated to afford 9 (18.5 g).

Step 6

To a solution of DMSO (7.98 g, 102 mmol) in $CH_2Cl_2$ (200 mL) at −78° C. was added oxalyl chloride (13.0 g, 102 mmol). The resultant solution was stirred at −78° C. for 30 min. The alcohol 9 (18.5 g, 78.7 mmol) in $CH_2Cl_2$ (50 mL) was then added to the solution of the oxidant. The resultant solution was stirred at −78° C. for 1 h. Triethyl amine (23.8 g, 236 mmol) was added to the solution and the resultant solution was stirred at −78° C. for 30 min. followed by stirring at room temperature for an additional 1 h. The solution was poured into 1 N NaOH and extracted with $CH_2Cl_2$ (3×). The combined organic layers were dried over $Na_2SO_4$, filtered, and concentrated to afford 10 (18 g) as a yellow oil.

Step 7

To a solution of aldehyde 9 (3.07 g, 13.2 mmol) in benzene (100 mL) was added amine 7 (3.91 g, 13.2 mmol) followed by benzotriazole 11 (1.57 g, 13.2 mmol). The solution was heated to reflux with a Dean-Stark trap attached for 7 h. The solution was concentrated to provide 12 (8.3 g) as a brown foam.

Step 8

To a solution of 12 (3.93 g, 6.2 mmol) in THF (100 mL) was added phenyl magnesium chloride (25 mmol). The solution was stirred at room temperature for 6 h. The solution was poured into a 25% sodium citrate solution and extracted with EtOAc (3×). The combined organic layers were washed with brine, dried over $Na_2SO_4$, filtered, and concentrated. The crude product was purified by prep TLC to afford diastereomer#1 700 mg (higher Rf by TLC) and 800 mg diastereomer#2 (lower Rf by TLC).

Step 9

To a solution of 13 diastereomer#1 (175 mg, 0.30 mmol) in MeOH (10 mL) was added 4M HCl (in dioxane). Stirred at room temperature for 3 h. The solution was concentrated and the crude product was partitioned between $CH_2Cl_2$ and $NaHCO_3$. The aqueous layer was extracted with $CH_2Cl_2$ (3×). The combined organic layers were dried over $Na_2SO_4$, filtered, and concentrated. The amine was dissolved in MeCN (2 mL). The pyrimidine acid (69 mg, 0.45 mmol), EDCI (87 mg, 0.45 mmol), HOBt (61 mg, 0.045 mmol), and $iPr_2NEt$ (194 mg, 1.50 mmol) were added. The solution was stirred at room temperature for 2 days. The solution was then concentrated. The crude product was partitioned between EtOAc and 1 M NaOH. The aqueous layer was extracted with EtOAc (3×). The combined organic layers were washed with brine, dried over $Na_2SO_4$, filtered, and concentrated. The crude product was purified by prep TLC (97:3 EtOAc: $Et_3N$) to afford 50 mg (27% yield) as a yellow oil.

Step 10

To a solution of the PMB amine 14 (50 mg, 0.08 mmol) in $CH_2Cl_2$ (2 mL) at 0° C. was added 1-chloroethyl chloroformate (15 mg, 0.10 mmol). The solution was stirred at 0° C. for 1 h. The solution was concentrated and the product was redissolved in MeOH (10 mL). The solution was heated to reflux for 45 min. The solution was then concentrated. The crude product was partitioned between $CH_2Cl_2$ and $NaHCO_3$. The aqueous layer was extracted with $CH_2Cl_2$ (3×). The combined organic layers were dried over $Na_2SO_4$, filtered, and concentrated to afford the amine 15 (41 mg) as a yellow oil.

Step 11

To a solution of the amine 15 (40 mg) in $CH_2Cl_2$ (1 mL) was added $Et_3N$ (12 mg, 0.12 mmol) and cyclopropyl sulfonyl chloride (13 mg, 0.10 mmol). The solution was stirred at room temperature for 16 h. Diluted with $CH_2Cl_2$. Added $NaHCO_3$ (aq.). The aqueous layer was extracted with $CH_2Cl_2$ (3×). The combined organic layers were dried over $Na_2SO_4$, filtered, and concentrated. The crude product was purified by prep TLC (5% $MeOH/CH_2Cl_2$) to afford the sulfonamide 16 (15 mg 31% yield) as a yellow oil.

The other compounds of the invention (e.g., those listed in Table 1 and Table 1A) could also be prepared by similar methods, using the variously applicable starting materials.

The following assays can be used to determine the CCR5 inhibitory and antagonistic activity of the compounds of the invention.

CCR5 Membrane Binding Assay:

A high throughput screen utilizing a CCR5 membrane binding assay identifies inhibitors of RANTES binding. This assay utilizes membranes prepared from NIH 3T3 cells expressing the human CCR5 chemokine receptor which have the ability to bind to RANTES, a natural ligand for the receptor. Using a 96-well plate format, membrane preparations are incubated with $^{125}$I-RANTES in the presence or absence of compound for one hour. Compounds are serially diluted over a wide range of 0.001 μg/ml to 1 μg/ml and tested in triplicates. Reaction cocktails are harvested through glass fiber filters, and washed thoroughly. Total counts for replicates are averaged and data reported as the concentration required to inhibit 50 percent of total $^{125}$I-RANTES binding. Compounds with potent activity in the membrane binding assay are further characterized in secondary cell-based HIV-1 entry and replication assays.

HIV-1 Entry Assay:

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by Connor et al, *Virology*, 206 (1995), p. 935-944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

HIV-1 Replication Assay:

This assay uses primary peripheral blood mononuclear cells or the stable U87-CCR5 cell line to determine the effect of anti-CCR5 compounds to block infection of primary HIV-1 strains. The primary lymphocytes are purified from normal healthy donors and stimulated in vitro with PHA and IL-2 three days prior to infection. Using a 96-well plate format, cells are pretreated with drug for 1 hour at 37° C. and subsequently infected with an M-tropic HIV-1 isolates. Following infection, the cells are washed to remove residual inoculum and cultured in the presence of compound for 4 days. Culture supernatants are harvested and viral replication measured by determination of viral p24 antigen concentration.

Calcium Flux Assay:

Cells expressing the HIV coreceptor CCR5 are loaded with calcium sensitive dyes prior to addition of compound or the natural CCR5 ligand. Compounds with agonist properties will induce a calcium flux signal in the cell, while the compounds of this invention are identified as compounds which do not induce signaling by themselves but are capable of blocking signaling by the natural ligand RANTES.

GTPγS Binding Assay (Secondary Membrane Binding Assay):

A GTPγS binding assay measures receptor activation by CCR5 ligands. This assay measures the binding of $^{35}$S labeled-GTP to receptor coupled G-proteins that occurs as a result of receptor activation by an appropriate ligand. In this assay, the CCR5 ligand, RANTES, is incubated with membranes from CCR5 expressing cells and binding to the receptor activation (or binding) is determined by assaying for bound $^{35}$S label. The assay quantitatively determines if compounds exhibit agonist characteristics by inducing activation of the receptor or alternatively antagonist properties by measuring inhibition of RANTES binding in a competitive or non-competitive fashion.

Chemotaxis Assay:

The chemotaxis assay is a functional assay which characterizes the agonist vs. antagonist properties of the test compounds. The assay measures the ability of a non-adherent murine cell line expressing human CCR5 (BaF-550) to migrate across a membrane in response to either test compounds or natural ligands (i.e., RANTES, MIP-1β). Cells migrate across the permeable membrane towards compounds with agonist activity. Compounds that are antagonists not only fail to induce chemotaxis, but are also capable of inhibiting cell migration in response to known CCR5 ligands.

Luciferase Replication Assay:

Plasmids encoding the full length genome of HIV-1 pNL-4-Luc with the gp 120 V-3 loop replaced by the Bgl II fragment of HIV-1 ADA, YU-2 or HxB (ADA-Luc-FL, YU-2-Luc-FL and HxB-Luc-FL) are obtained from Dr. Susan Pontow (Washington University, St. Louis Mo.). Replication-competent luciferase reporter virus stocks are generated by transfection of plasmids into 293T cells using Superfect (Qiagen) or Mirus transfection reagents. Viral stocks are collected 48 hours following transfection and titered for luciferase production on U-87-CCR5 or CXCR4 cells. U87-CD4-CCR5 cells ($10^4$/ well) are plated in 96-well cell culture plates and incubated overnight. Media is removed and replaced with 50 μl of fresh culture media (DMEM, 10% FCS) and 50 μl of compound diluted in culture medium. Cells are incubated with compound at 37° C. for 1 hour. The resultant supernatant is removed and replaced with 20 μl of media containing compound and infected with an equal volume of diluted or undiluted virus stock at 37° C. for 3-4 hours. The cells are washed once with DMEM, and 200 μl of media containing compound is added. The cultures are incubated for 3 days, the cells lysed in luciferase lysis buffer (Promega, Madison, Wis.) and transferred to Immulon plates (Dynex Technologies, Chantilly Va.). An equal volume of luciferase substrate (Promega, Madison Wis.) is added to lysates and the plates read immediately in a Wallac Luminometer. Fifty and ninety percent inhibitory concentrations are determined using GraphPad PRISM software.

| Example | Structure | HIV Replication (Luciferase) IC$_{50}$ nM | HRMS Found (MH$^+$) |
|---|---|---|---|
| 1 | 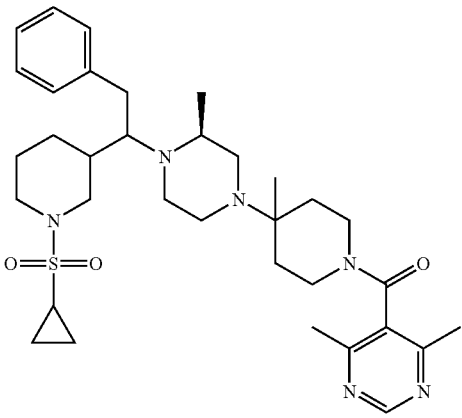 1:1 mixture of diastereomers | 2 | 623.3750 |
| 2 | 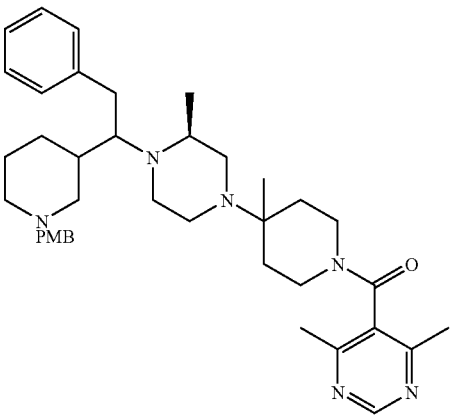 1:1 mixture of diastereomers | 25 | 639.4394 |
| 3 | 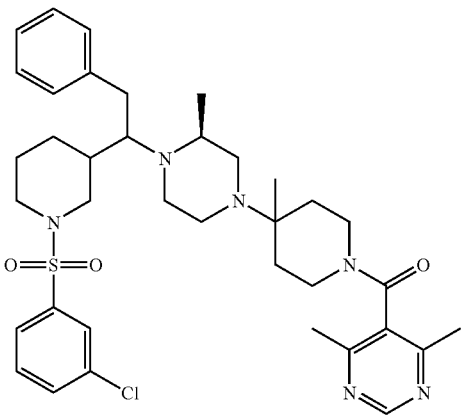 1:1 mixture of diastereomers | 2 | 693.3362 |

-continued

| Example | Structure | HIV Replication (Luciferase) IC$_{50}$ nM | HRMS Found (MH$^+$) |
|---|---|---|---|
| 4 | *1:1 mixture of diastereomers* | 4 | 519.3818 |
| 5 | *Diastereomer #1* | 15 | 631.3437 |
| 6 | *Diastereomer #2* | 0.7 | 631.3437 |

-continued
| Example | Structure | HIV Replication (Luciferase) IC$_{50}$ nM | HRMS Found (MH$^+$) |
|---|---|---|---|
| 7 | 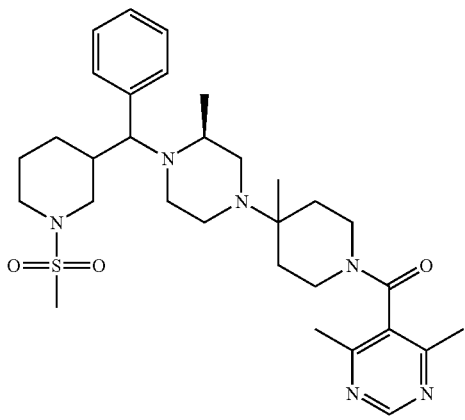<br>Diastereomer #1 | 0.5 | 605.3278 |
| 8 | 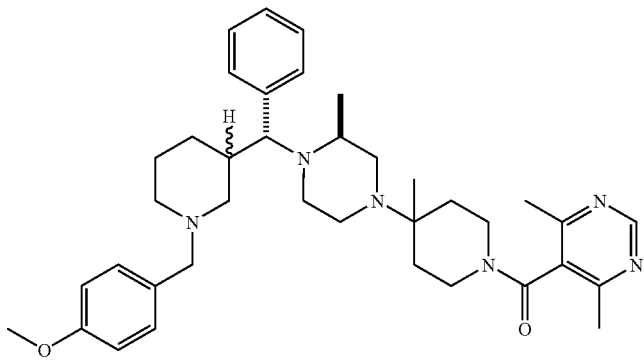<br>1/1 mix of diastereomers | 1.6 | 625.4240 |
| 9 | 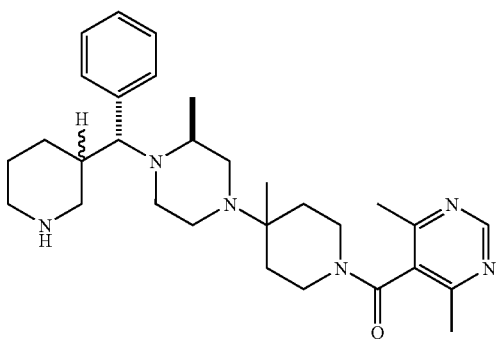<br>1/1 mix of diastereomers | 11 | 505.3655 |

-continued

| Example | Structure | HIV Replication (Luciferase) IC$_{50}$ nM | HRMS Found (MH$^+$) |
|---|---|---|---|
| 10 | 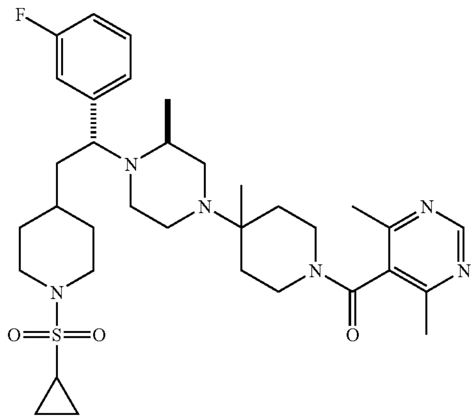 | 3 | 641.3655 |
| 11 | 1/1 mix of diastereomers | 0.3 | 613.3333 |
| 12 | 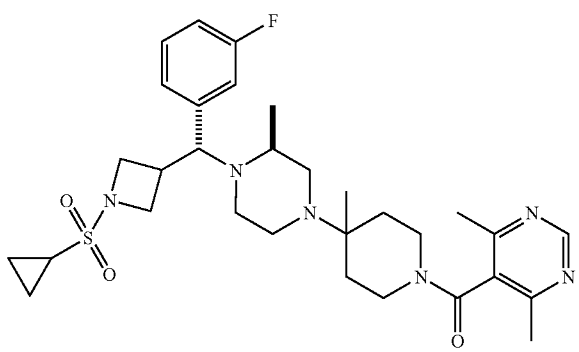 | 1 | 599.3207 |
| 13 | 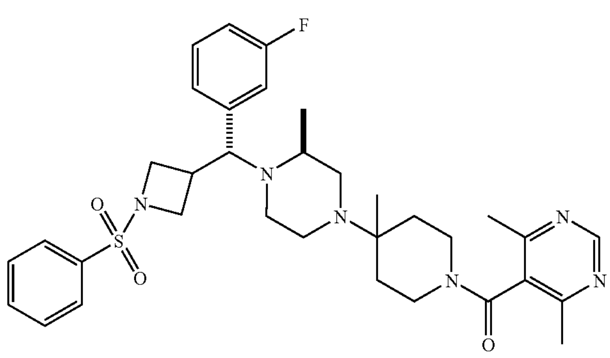 | 0.7 | 635.3191 |

-continued

| Example | Structure | HIV Replication (Luciferase) IC$_{50}$ nM | HRMS Found (MH$^+$) |
|---------|-----------|-------------------------------------------|---------------------|
| 14 | 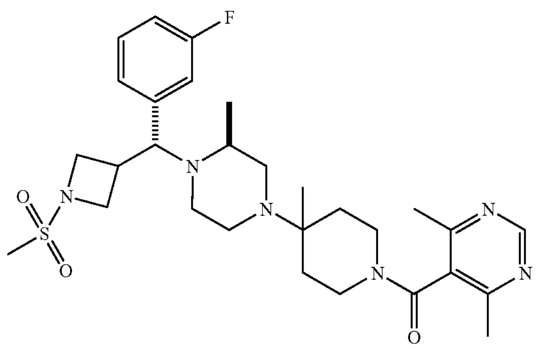 | 2 | 573.3026 |
| 15 | 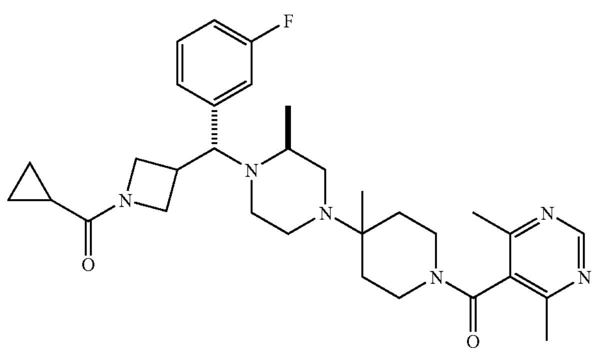 | 5 | 563.3515 |
| 16 | 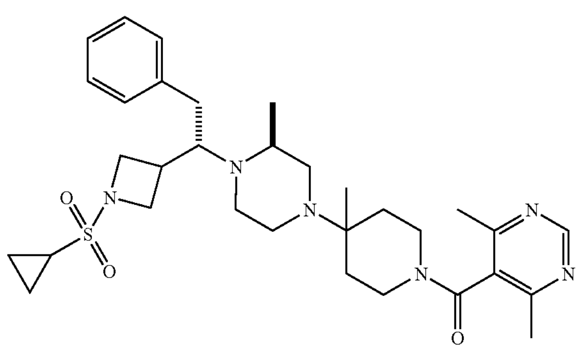 | 4 | 595.3416 |
| 17 | 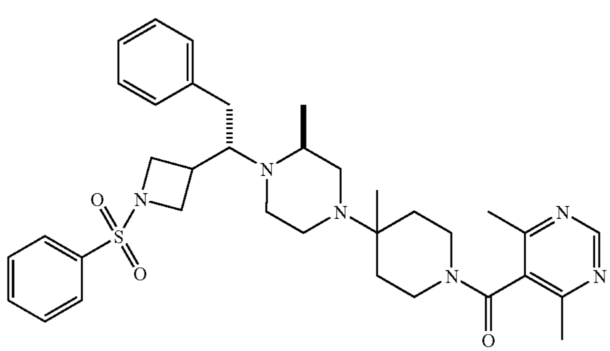 | 0.4 | 631.6452 |

-continued

| Example | Structure | HIV Replication (Luciferase) IC$_{50}$ nM | HRMS Found (MH$^+$) |
|---|---|---|---|
| 18 | 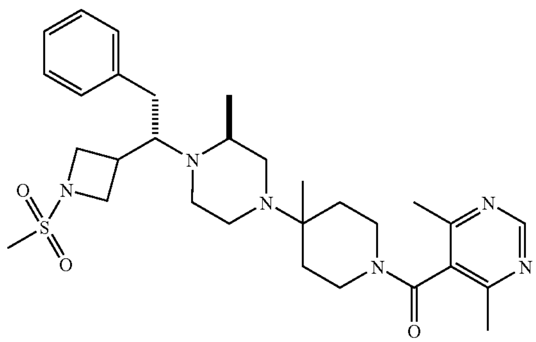 | 17 | 569.3261 |
| 19 | 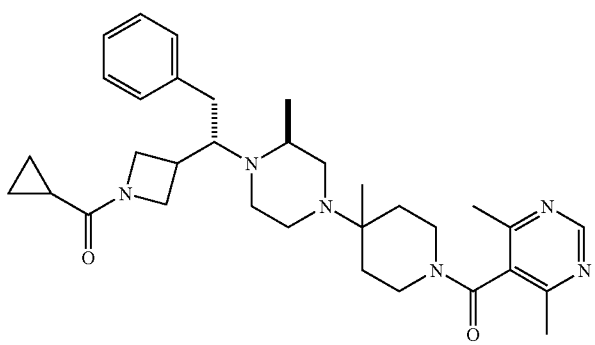 | 13 | 559.3769 |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by structural formula I:

Formula I

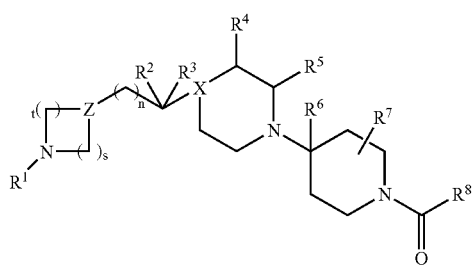

or a pharmaceutically acceptable salt or solvate thereof; wherein:

n is 0, 1, 2, 3 or 4;
s is 0, 1, 2, 3 or 4;
t is 1, 2, 3 or 4 with the provisos that i) when n is 0 and s is 2, then t is 1, 3 or 4; and
ii) when n is 0 and t is 2, then s is 0, 1, 3 or 4;

X is N;

Z is N or CH;

$R^1$ is H, alkyl, aralkyl, —S(O$_2$)alkyl, —S(O$_2$)aryl, —C(O)alkyl, —C(O)aryl, -alkyl-aryl-R$^8$, -alkyl-heteroaryl- R$^8$, —S(O$_2$)cycloalkyl, —S(O$_2$)-aryl-R$^8$, —C(O)cycloalkyl, —C(O)-aryl-R$^8$, —C(O)NR$^{20}$R$^{21}$ or —S(O$_2$)NR$^{20}$R$^{21}$;

$R^2$, $R^4$, $R^5$, $R^6$ and $R^7$ can be the same or different each being independently H or alkyl;

$R^3$ is H, alkyl, cycloalkyl, aralkyl, heteroaralkyl, aryl or heteroaryl;

or $R^2$ and $R^3$ taken together are =N(O-alkyl), =N(OH), =N—N(R$^{20}$R$^{21}$) or =CH(alkyl) provided that when one or both of X and Z is N, $R^2$ and $R^3$ together are not =CH(alkyl);

$R^8$ is aryl, heteroaryl, fluorenyl; and diphenylmethyl, heteroaryl-N-oxide,

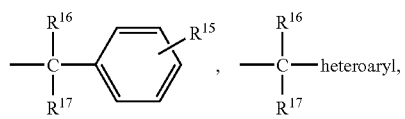

-continued

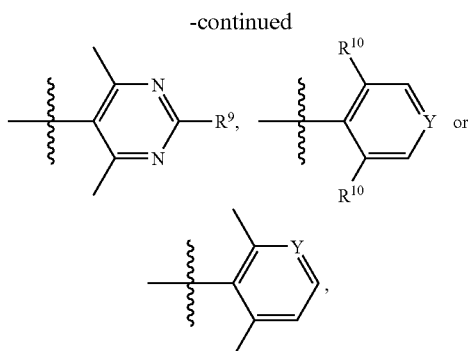

wherein each $R^{10}$ is the same or different and independently selected from —$CH_3$ or halogen, Y is N or N(→O) and each of said aryl, fluorenyl, diphenyl and heteroaryl is unsubstituted or optionally independently substituted with 1 to 4 substituents which substituents can be the same or different each being independently selected from the group consisting of $R^{11}$, $R^{12}$, $R^{13}$, $R^{14}$ and $R^{15}$;

$R^9$ is H, alkyl, —$CF_3$, cycloalkyl, —OH, —$OCH_3$, —$NH_2$, —N(H)C(O)N(H)alkyl, —$NHS(O_2)R^{20}$ or —N(H)C(O)alkyl;

$R^{11}$ and $R^{12}$ can be the same or different and are each independently selected from the group consisting of alkyl, haloalkyl, halogen, —$NR^{18}R^{19}$, —OH, —$CF_3$, —$OCH_3$, —O-acyl and —$OCF_3$;

$R^{13}$ is selected from the group consisting of H, $R^{11}$, aryl, —$NO_2$, —CN, —$CH_2F$, —$CHF_2$, —C(O)H, —CH=$NOR^{18}$, pyridyl-N-oxide, pyrimidinyl, pyrazinyl, —$N(R^{19})CONR^{19}R^{20}$, —N(H)C(O)N(H)(haloalkyl), —N(H)C(O)N(H)(cycloalkylalkyl), —N(H)C(O)alkyl, —N(H)C(O)$CF_3$, —$N(H)S(O_2)N(alkyl)_2$, —$N(H)S(O_2)$alkyl, —$N(S(O_2)CF_3)_2$, —N(H)C(O)Oalkyl, cycloalkyl, —$SR^{21}$, —$S(O)R^{21}$, —$S(O_2)R^{21}$, —$S(O_2)N(H)$(alkyl), —$OS(O_2)$alkyl, —$OS(O_2)CF_3$, hydroxyalkyl, —$C(O)NR^{18}R^{19}$, —C(O)N($CH_2CH_2$—O—$CH_3$)$_2$, —OC(O)N(H)alkyl, —$CO_2R^{18}$, —Si($CH_3$)$_3$ and —$B(OC(CH_3)_2)_2$;

$R^{14}$ is selected from the group consisting of alkyl, haloalkyl, $NH_2$ and $R^{15}$-phenyl;

$R^{15}$ is 1 to 3 substituents selected from the group consisting of H, alkyl, haloalkyl, —$CF_3$, —$CO_2R^{19}$, —CN, alkoxy and halogen; wherein said $R^{15}$ moieties can be the same or different each being independently selected when there are more than one $R^{15}$ present;

$R^{16}$ and $R^{17}$ can be the same or different each being independently selected from the group consisting of hydrogen and alkyl, or $R^{16}$ and $R^{17}$ together are an alkylene group and with the carbon to which they are attached form a spiro ring of 3 to 6 carbon atoms;

$R^{18}$, $R^{19}$ and $R^{20}$ can each be the same or different and are each independently selected from the group consisting of H, alkyl, cycloalkyl, aryl and heteroaryl; and $R^{21}$ is selected from the group consisting of alkyl, haloalkyl, hydroxyalkyl, alkylene, cycloalkyl, aryl and aralkyl;

wherein each of said alkyl, alkylene, aryl, arylalkyl, aralkyl, alkoxy, hydroxyalkyl, heteroaryl, heteroaralkyl, cycloalkylalkyl and cycloalkyl in the definitions above can be unsubstituted or optionally independently substituted with one or more moieties which can be the same or different, where said moieties are independently selected from the group consisting of —OH, alkoxy, —CN, halogen, —$NR^{18}R^{19}$, —C(O)$NR^{18}R^{19}$, —$N(R^{18})C(O)R^{19}$, —$N(R^{18})S(O_2)R^{19}$, —$S(O_2)NR^{18}R^{19}$, —$C(O)OR^{18}$, —$OCF_3$, —$CF_3$, —$S(O_2)R^{18}$ and —$C(O)R^{18}$.

2. A compound according to claim 1, wherein n is 0.

3. A compound according to claim 1 wherein $R^4$ and $R^7$ are alkyl.

4. A compound according to claim 3 wherein $R^4$ and $R^7$ are methyl.

5. A compound according to claim 1 wherein $R^1$ is H, —$S(O_2)$alkyl, —$S(O_2)$aryl or —$S(O_2)$cycloalkyl.

6. A compound according to claim 1 wherein $R^1$ is H,

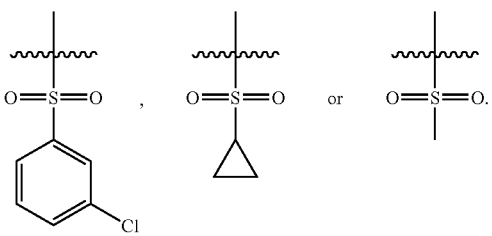

7. A compound according to claim 1 wherein $R^3$ is aryl or aralkyl.

8. A compound according to claim 7 wherein $R^3$ is benzyl or phenyl.

9. A compound according to claim 1 wherein $R^8$ is heteroaryl.

10. A compound according to claim 1 wherein $R^8$ is

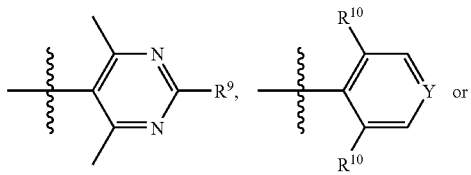

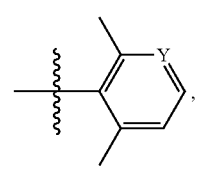

wherein each $R^{10}$ is the same or different and independently selected from —$CH_3$ or halogen, Y is N or N(→O) and each of said aryl, fluorenyl, diphenyl or heteroaryl is unsubstituted or optionally independently substituted with 1 to 4 substituents each of which substituents can be the same or different and is independently selected from the group consisting of $R^{11}$, $R^{12}$, $R^{13}$, $R^{14}$ and $R^{15}$.

11. A compound having the structural formula I according to claim 1 wherein $R^1$ and $R^3$ are as defined in the following table:
| $R^1$ | $R^3$ |
|---|---|
| cyclopropylsulfonyl | benzyl |
| PMB | benzyl |
| 3-chlorophenylsulfonyl | benzyl |
| H | benzyl |
| cyclopropylsulfonyl | phenyl |
| cyclopropylsulfonyl | phenyl |
12. A compound according to claim 1 represented by the structural formulae:
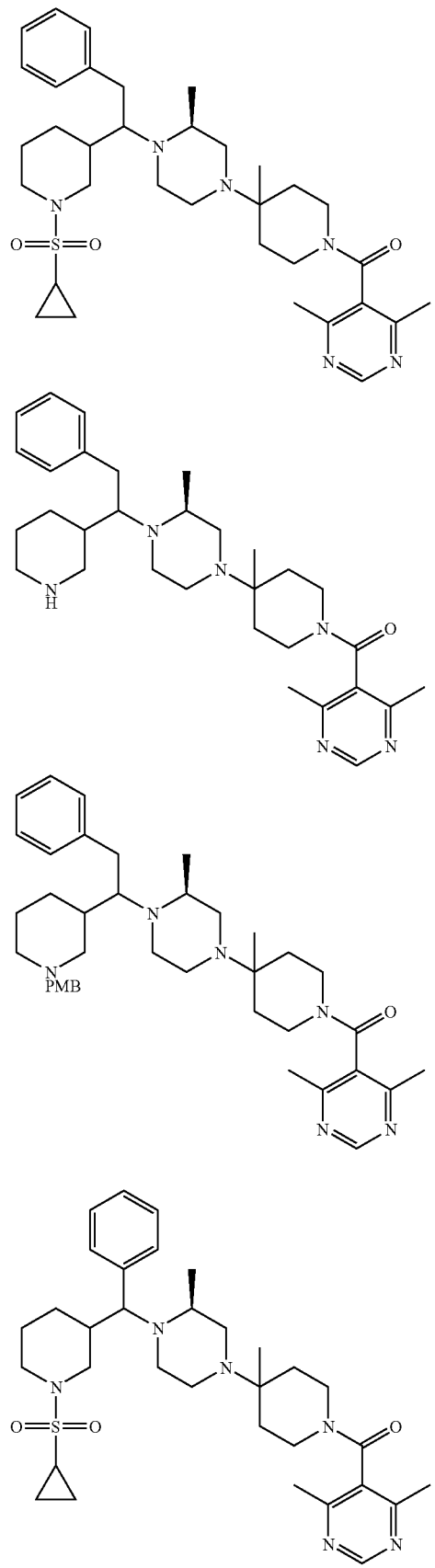

-continued
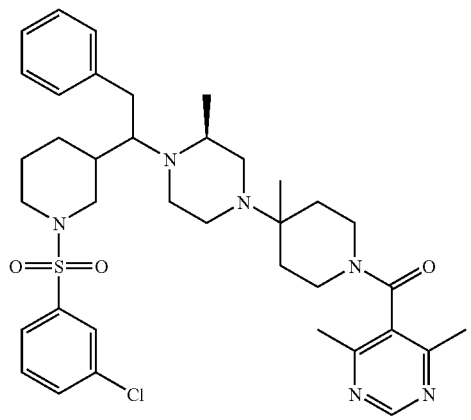
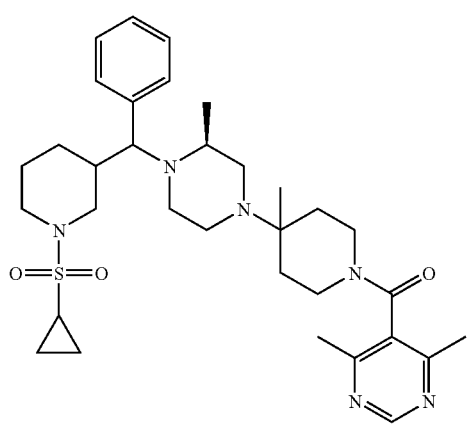
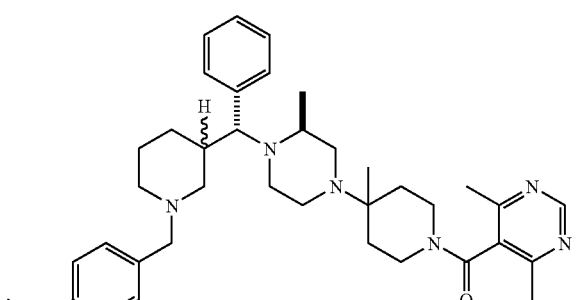
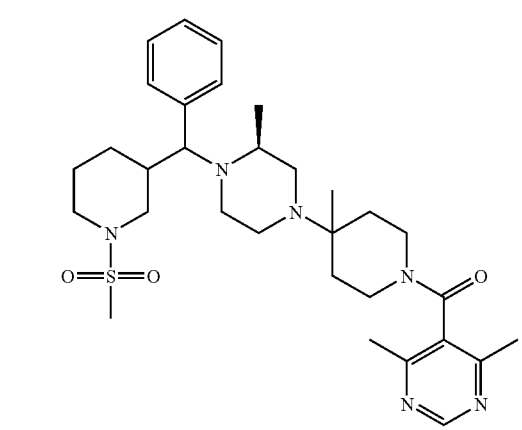
-continued
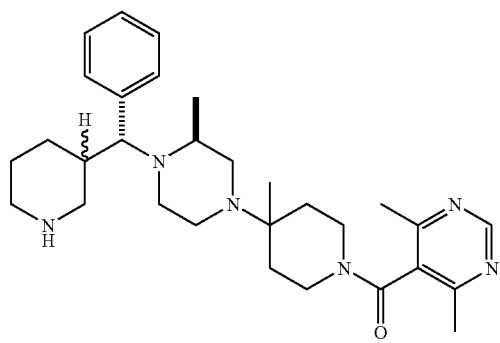
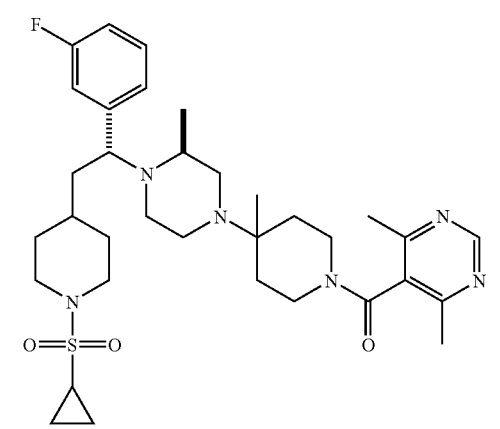
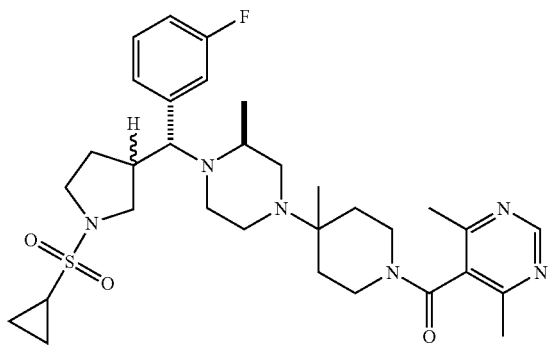
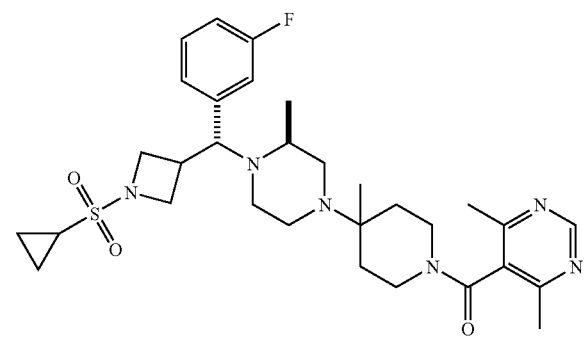

-continued

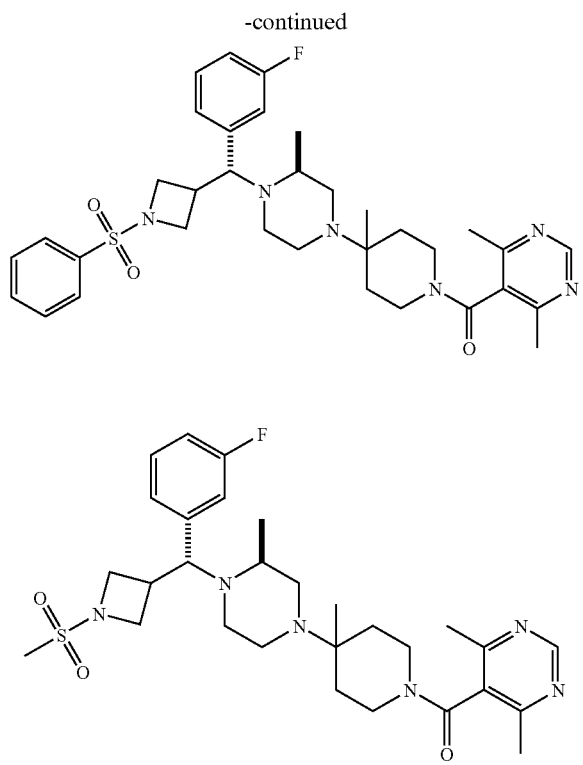

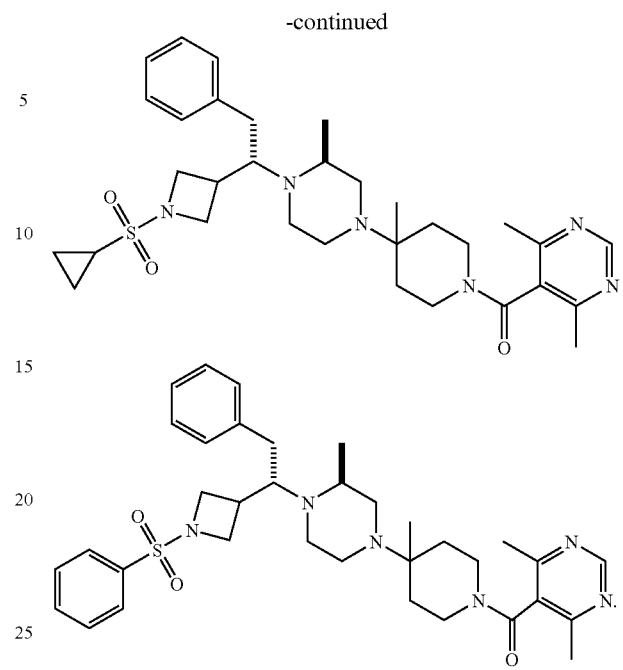

13. A pharmaceutical composition comprising a therapeutically effective amount of one or more compounds of claim 1.

14. A pharmaceutical composition comprising a therapeutically effective amount of one or more compounds of claim 12.

15. The pharmaceutical composition according to claim 13 further comprising one or more pharmaceutically acceptable carriers.

16. The pharmaceutical composition according to claim 14 further comprising one or more pharmaceutically acceptable carriers.

17. A process for making a pharmaceutical composition, comprising combining at least one compound of claim 1, and at least one pharmaceutically acceptable carrier.

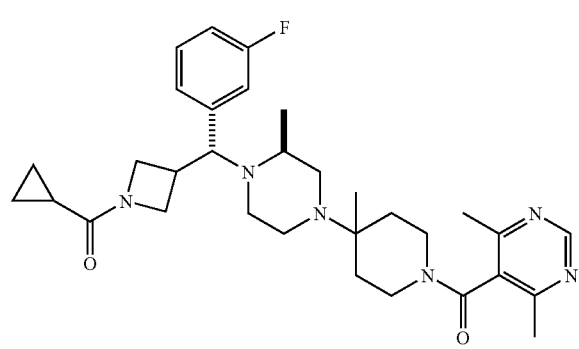

* * * * *